Figure 1:
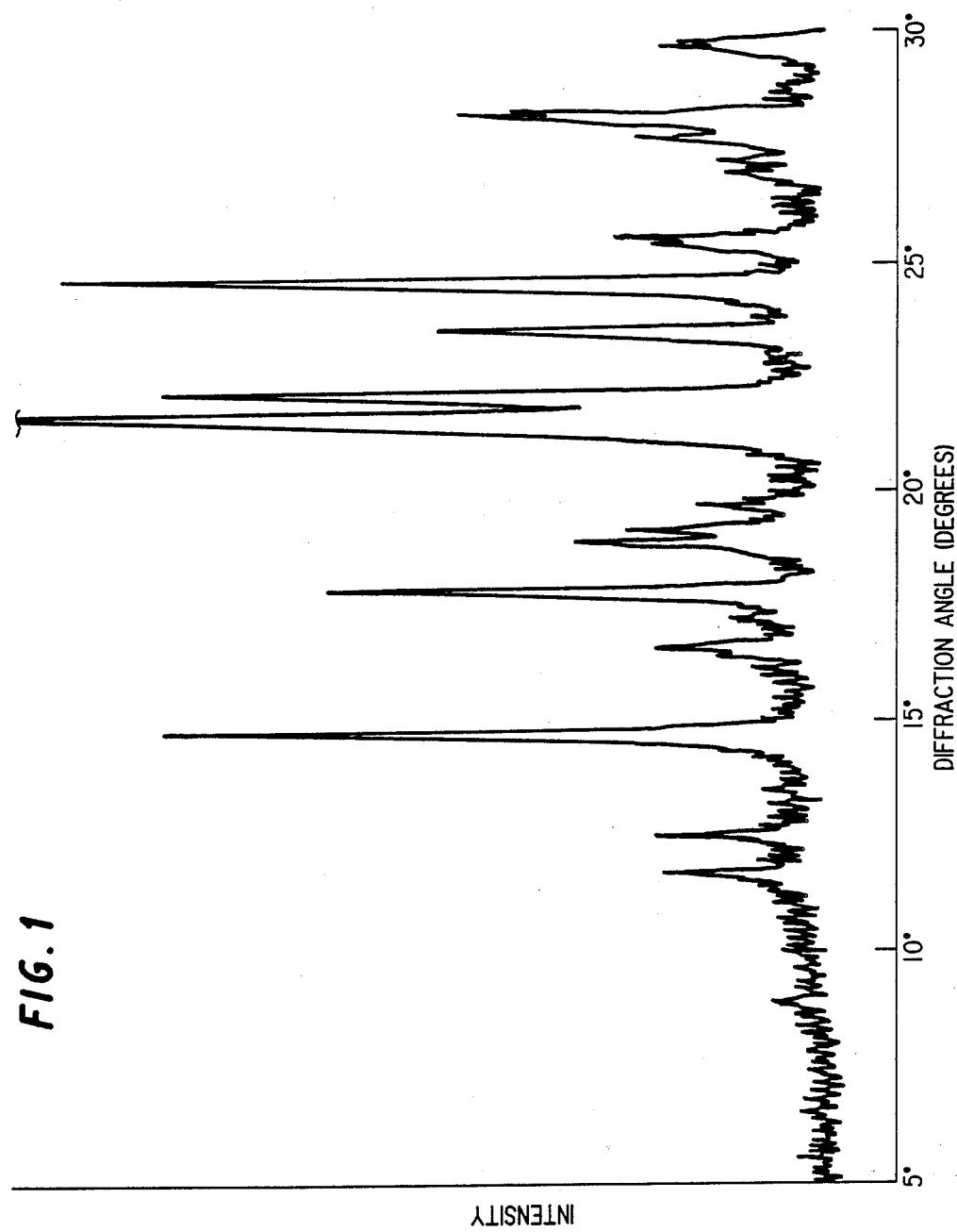

United States Patent [19]

Takaya et al.

[11] Patent Number: 4,935,507

[45] Date of Patent: Jun. 19, 1990

[54] CRYSTALLINE 7-(2-(2-AMINOTHIAZOL-4-YL)-2-HYDROX-YIMINOACETAMIDO)-3-VINYL-3-CEPHEM-4-CARBOXYLIC ACID (SYN ISOMER)

[75] Inventors: Takao Takaya, Kawanishi; Fumiyuki Shirai, Ikeda; Hitoshi Nakamura, Mino; Yasunobu Inaba, Toyonaka, all of Japan

[73] Assignee: Fujisawa Pharmaceutical Co., Ltd., Osaka, Japan

[21] Appl. No.: 229,489

[22] Filed: Aug. 8, 1988

[30] Foreign Application Priority Data

Aug. 19, 1987 [JP] Japan .................................. 62-206199

[51] Int. Cl.$^5$ ................ C07D 501/124; A61K 31/545

[52] U.S. Cl. .................................................. 540/222
[58] Field of Search ...................... 540/229, 222, 226; 514/202

[56] References Cited

U.S. PATENT DOCUMENTS 4,559,334 12/1985 Takaya et al. ..................... 514/202

Primary Examiner—Nicholas S. Rizzo
Attorney, Agent, or Firm—Oblon, Spivak, McClelland, Maier & Neustadt

[57] ABSTRACT

The invention relates to crystalline 7-[2-(2-aminothiazol-4-yl)-2-hydroxyiminoacetamido]-3-vinyl-3-cephem-4-carboxylic acid (syn isomer) useful as an antimicrobial agent.

5 Claims, 2 Drawing Sheets

CRYSTALLINE 7-(2-(2-AMINOTHIAZOL-4-YL)-2-HYDROXYIMINOACETAMIDO)-3-VINYL-3-CEPHEM-4-CARBOXYLIC ACID (SYN ISOMER)

The present invention relates to novel crystalline 7-[2-(2-aminothiazol-4-yl)-2-hydroxyiminoacetamido]-3-vinyl-3-cephem-4-carboxylic acid (syn isomer) [hereinafter referred to as "the compound (I)" in the present specification] as shown by the following formula (I):

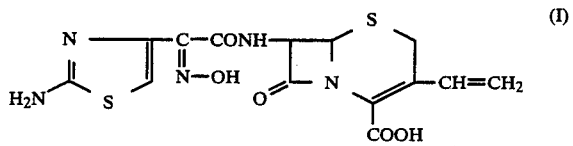

The compound (I), which is a very useful antimicrobial agent, is a known compound and was described, for example, in U.S. Pat. No. 4,559,334 as the object compounds of Examples 14 and 16.

Our further experimental investigation revealed that the compound (I) each prepared according to the procedures of said Examples 14 and 16 in said U.S. Patent was a crystalline like amorphous product, not a crystalline product. However, the amorphous product has disadvantages that it is bulky, not so pure, unstable and insufficient in filtration rate, therefore it is not suitable for a pharmaceutical product or is not easy to handle in the pharmaceutical preparations, in producing it in a large scale or in storage.

After an intensive study, the inventors of the present invention succeeded in obtaining the compound (I) as a special crystalline form, i.e. Crystal A and completed the present invention, which is explained in detail as follows.

Physicochemical Properties of Crystal A of The Compound (I)

The physicochemical properties of Crystal A of the compound (I) provided by the present invention are explained in the following.

(1) Crystal Form prisms

(2) Powder X-Ray Diffraction Pattern

Crystal A of the compound (I) shows its distinguishing peaks at the diffraction angles [$2\theta(°)$] as shown in the following table.

| $2\theta(°)$ |
| --- |
| about 14.7 |
| about 17.8 |
| about 21.5 |
| about 22.0 |
| about 23.4 |
| about 24.5 |
| about 28.1 |

In FIG. 1, a chart of powder X-ray diffraction pattern of Crystal A of the compound (I) obtained in Example 4 described later is shown.

But this diffraction pattern is given only for a reference and any crystal of the compound (I) which shows substantially the same diffraction pattern is identified as Crystal A of the compound (I).

(3) Infrared Absorption Spectrum

Figure 2:
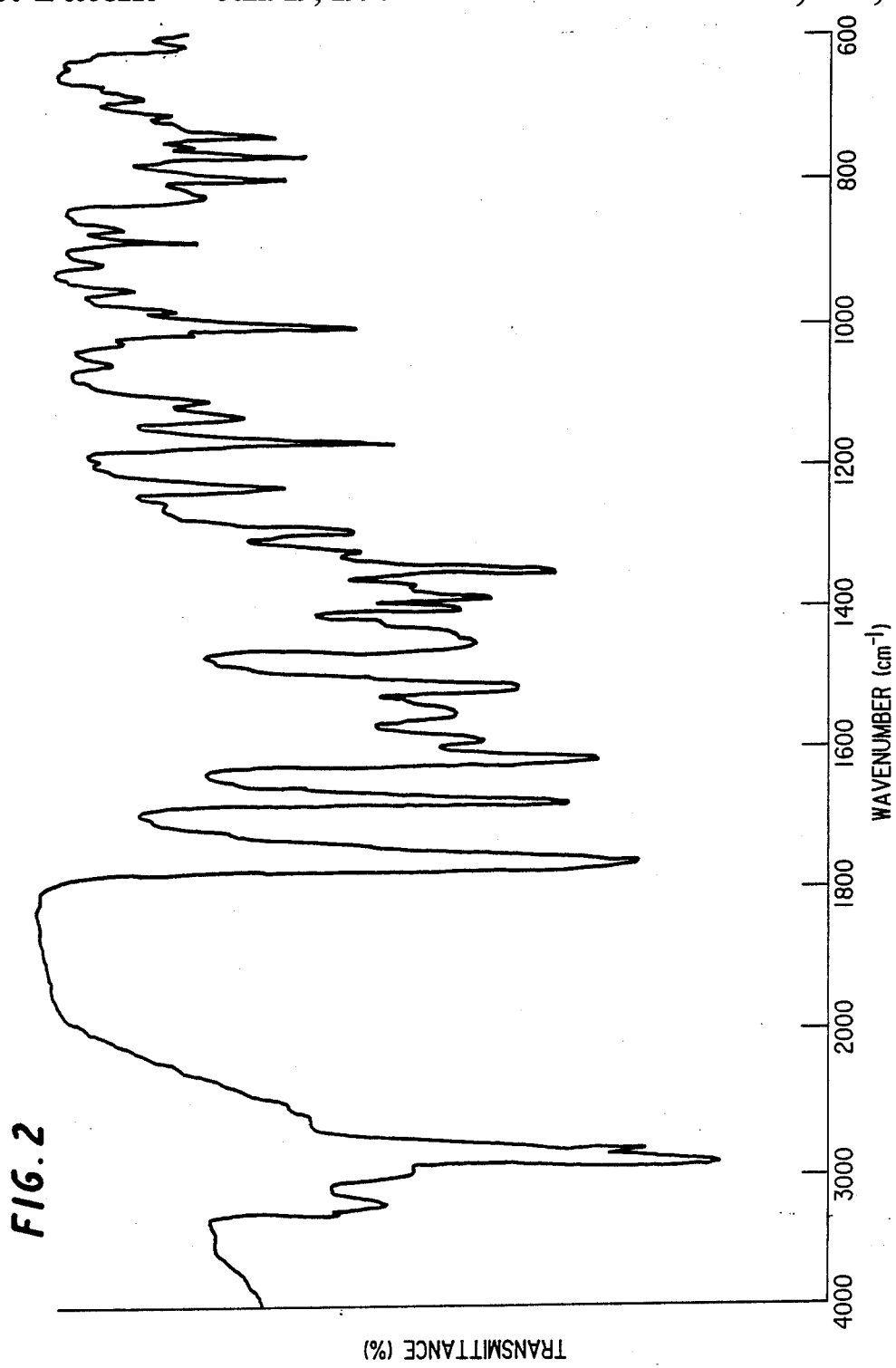

In FIG. 2, a chart of infrared absorption spectrum of Crystal A of the compound (I) obtained in Example 4 described later is shown.

But this spectrum is given only for a reference and any crystal of the compound (I) which shows substantially the same spectrum is identified as Crystal A of the compound (I).

The Process For Preparing Crystal A of The Compound (I)

In the following, the process for the preparation of Crystal A of the compound (I) of the present invention is explained in detail.

Crystal A of the compound (I) can be obtained by acidifying the solution containing the compound (I) at room temperature or under warming and thereby having the crystals separate out of the solution.

Suitable examples of "the solution containing the compound (I)" may include, for example, an aqueous solution of the alkali metal salt of the compound (I).

The solution containing the compound (I) is acidified, if necessary, after said solution is subjected to a column chromatography on activated charcoal, nonionic adsorption resin, alumina, acidic aluminium oxide. This acidifying process can be carried out by adding an acid such as hydrochloric acid or the like preferably in the temperature range from room temperature to 40° C., more preferably, from 15° to 40° C. The amount of the acid to be added is preferably the one which makes the pH value of the solution from 1 to 4.

Crystal A of the compound (I) can be also obtained by dissolving the compound (I) in an alcohol (preferably methanol), continuing to stir this solution slowly under warming (preferably below 40° C.), preferably after the addition of water warmed at almost the same temperature as that of said solution, then cooling this solution to room temperature and allowing it to stand.

During the crystallization of Crystal A, it is preferable to keep the condition of slightly beyond the saturation.

Crystal A of the compound (I) obtained according to aforesaid process can be collected by filtration and dried by means of the conventional methods.

The water content of Crystal A of the compound (I) obtained above is about 0.8% (measured by Karl Fisher method).

The Advantage of The Crystal A of The Compound (I)

The Crystal A of the compound (I) is not bulky, is very pure and is very stable against heat, light and the like. Therefore, the Crystal A of the compound (I) is suitable for a pharmaceutical product and is easy to handle in the pharmaceutical preparations and in storage.

Further, the Crystal A of the compound (I) has sufficient filtration rate and the operation efficiency in case of producing it is very high. Therefore the Crystal A of the compound (I) is very suitable to produce even in a large scale such as a laboratory scale.

Moreover, due to its ease to be filtered, impurities are difficult to mix in the purification step. Therefore, the compound (I) with high quality can be produced.

As stated above, the Crystal A of the compound (I) possesses very good advantage and much superior to the amorphous product of the compound (I).

In order to show said advantage of the Crystal A of the compound (I), the comparative test results on stability between the Crystal A of the compound (I) and the compound (I) given by aforesaid U.S. Pat. No. 4,559,334 are shown in the following.

Test Sample

Sample 1—the compound (I) obtained in Example 14 in said U.S. Patent

Sample 2—the compound (I) obtained in Example 16 in said U.S. Patent

Sample A—Crystal A of the compound (I) of the present invention

Test Method

The stability of each test sample was examined under the condition of 50° C. in a closed container.

Color of the solution of each sample was determined by measuring transmittance at 510 nm with spectrophotometer(T %) (1% solution in 1% $NaHCO_3$ aqueous solution was used).

The potency of each sample was determined by liquid chromatography and the residual percentage to the initial value was calculated.

| Test Sample | Test Item | Test Results Initial | After 1 day | After 7 days |
|---|---|---|---|---|
| Sample 1 | appearance | pale brownish yellow powder | pale brownish yellow powder | brownish yellow powder |
| | color of the solution(T%) | 47.0 | 39.2 | 25.5 |
| | potency (%) | 100 | 97.2 | 85.1 |
| Sample 2 | appearance | yellow powder | yellow powder | brownish yellow powder |

| Test Sample | Test Item | Test Results Initial | After 1 day | After 7 days |
|---|---|---|---|---|
| | color of the solution(T%) | 63.8 | 54.5 | 37.3 |
| | potency (%) | 100 | 89.3 | 52.4 |
| Sample A | appearance | yellowish white crystal | yellowish white crystal | yellowish white crystal |
| | color of the solution(T%) | 98.9 | 98.9 | 98.7 |
| | Potency (%) | 100 | 99.8 | 99.4 |

As shown in the test results, there was slight change in the appearance of Samples 1 and 2, while there was no change in the appearance of Sample A.

Further, there was significant lowering of the transmittance (T %) in case of Samples 1 and 2, while there was almost no lowering in case of Sample A.

These results indicated that Samples 1 and 2 were much easier to discolor than Sample A.

Further, as shown in the test results, the potency of Samples 1 and 2 apparently decreased, while the potency of Sample A was almost unchanged.

As stated above, only after 7 days there appeared much difference regarding the stability between the Crystal A of the compound (I) and the compound (I) given by U.S. Pat. No. 4,559,334.

Namely, it turned out that the Crystal A of the compound (I) was much superior to the compound (I) given by said U.S. Patent.

Next, the process for preparing the compound (I) used in the present invention is explained in detail.

Process For Preparing The Compound (I)

The compound (I) or a salt thereof can be prepared by the method disclosed in U.S. Pat. No. 4,559,334 as mentioned before, but in order to obtain the compound (I) at higher yield, it is preferable to use the method as shown in the following reaction schemes.

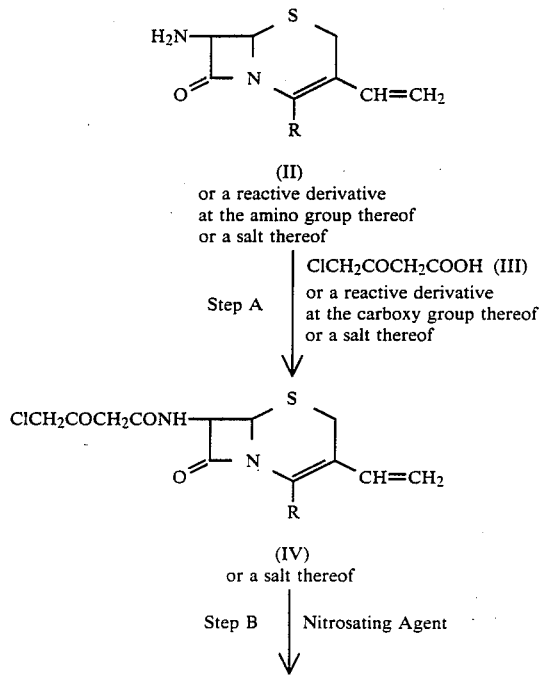

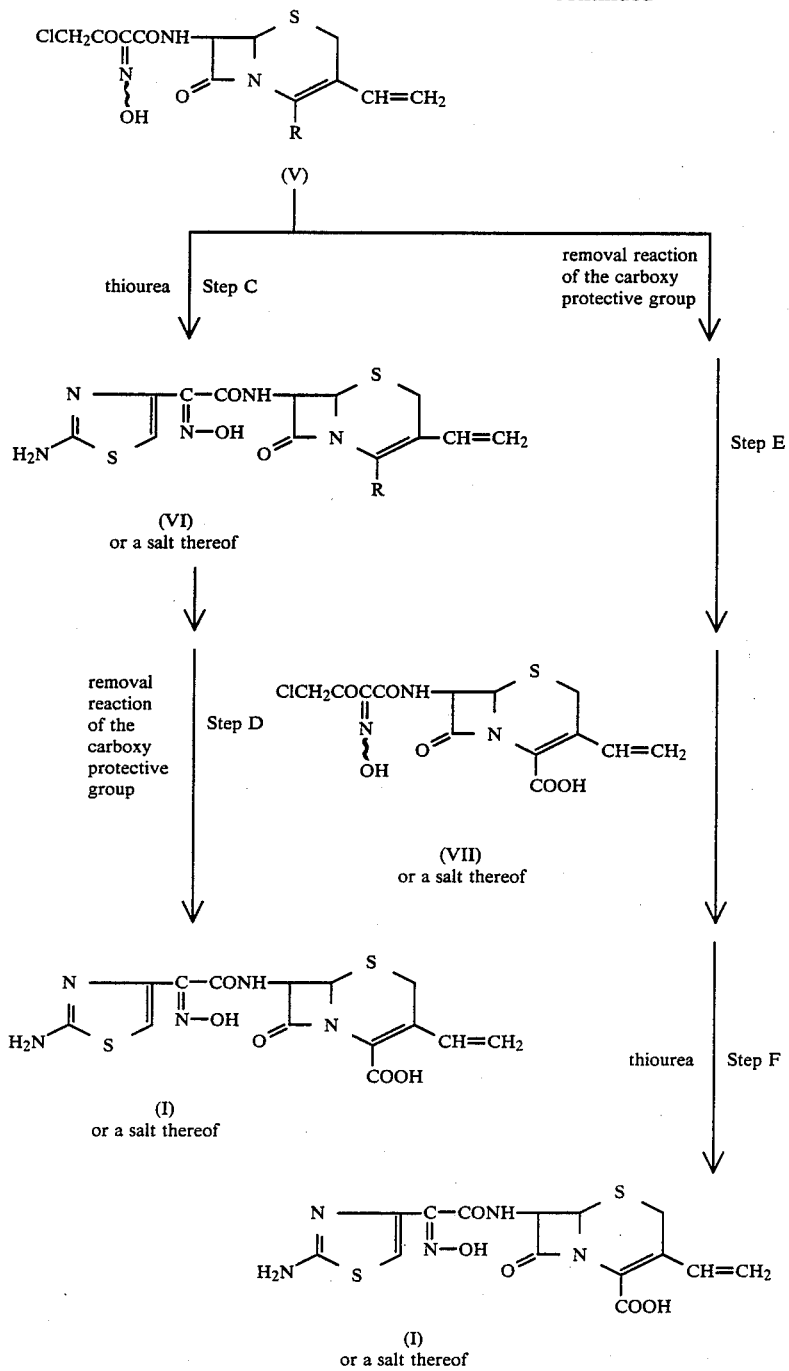

wherein R is a protected carboxy group.

Suitable "a protected carboxy group" in aforesaid R may include the ones which are used conventionally in cephalosporin compound, for example, esterified carboxy, and the like.

Suitable examples of said "esterfied carboxy" may include ar(loweralkoxycarbonyl such as benzyloxycarbonyl, benzhyeryloxycarbonyl, trityloxycarbonyl or the like, and the like.

Suitable salts of the compound (I) are conventional non-toxic salts and may include a salt with a base or an acid addition salt such as a salt with an inorganic base, for example, an alkali metal salt (e.g. sodium salt, potassium salt, etc.), an alkaline earth metal salt (e.g. calcium salt, magnesium salt, etc.), an ammonium salt; a salt with an organic base, for example, an organic amine salt (e.g. triethylamine salt, pyridine salt, picoline salt, ethanolamine salt, triethanolamine salt, dicyclohexylamine salt, N,N'-dibenzylethylenediamine salt, etc.) etc.; an inorganic acid addition salt (e.g. hydrochloride, hydrobromide, sulfate, phosphate, etc.); an organic acid addition salt, for example, an organic carboxylic or sulfonic acid addition salt (e.g. formate, acetate, trifluoroacetate, maleate, tartrate, methanesulfonate, benzenesulfonate, p-toluenesulfonate, etc.); an organic phosphonic acid addition salt [e.g. 3-(N-formyl-N-hydroxyamino)- propylphosphonate, 2-hydroxy-8-(N-hydroxyamino)-propylphosphonate, etc.], etc.; a salt with a basic or acidic amino acid (e.g. arginine, aspartic acid, glutamic acid, etc.); and the like.

The process for preparing aforesaid compound (I) is explained in detail in the following.

Step A

The compound (IV) or a salt thereof can be produced by reacting the compound (II) or a reactive derivative at the amino group thereof, or a salt thereof with the compound (III) or a reactive derivative at the carboxy group thereof or a salt thereof.

Suitable reactive derivative at the amino group of the compound (II) may include a conventional one, for example, a silyl derivative formed by the reaction of the compound (II) with a silyl compound such as trimethylsilylacetamide, bis(trimethylsilyl)acetamide, bis(trimethylsilyl)urea, and the like, and suitable reactive derivative at the carboxy group of the compound (III) may include an acid halide such as acid chloride, acid bromide, or the like, which can be prepared by the reaction of diketene and halogen.

Suitable salt of the compound (II) may include the acid addition salt as exemplified for the compound (I), and suitable salt of the compound (III) may include the same salt with a base as exemplified for the compound (I).

The reaction is usually conducted in a conventional solvent which does not adversely influence the reaction such as water, acetone, dioxane, acetonitrile, chloroform, benzene, carbon tetrachloride, methylene chloride, ethylene chloride, tetrahydrofuran, ethyl acetate, N,N-dimethylformamide, N,N-dimethylacetamide, pyridine, hexamethylphosphoramide, etc., or a mixture thereof.

The reaction temperature is not critical and the reaction is usually conducted under cooling to warming.

Step B

The compound (V) can be produced by reacting the compound (IV) or a salt thereof with a nitrosating agent.

Suitable nitrosating agent may include nitrous acid and its conventional derivatives such as nitrosyl halide (e.g. nitrosyl chloride, nitrosyl bromide, etc.), alkali metal nitrite (e.g. sodium nitrite, potassium nitrite, etc.), alkyl nitrite (e.g. butyl nitrite, pentyl nitrite, isoamyl nitrite, etc.), and the like.

In case that a salt of nitrous acid, for example, its alkali metal salt is used as a nitrosating agent, the reaction is preferably carried out in the presence of an acid such as an inorganic or organic acid (e.g. hydrochloric acid, sulfuric acid, formic acid, acetic acid, etc.).

This reaction is usually conducted in a conventional solvent which does not adversely influence the reaction such as water, acetic acid, benzene, methanol, ethanol, tetrahydrofuran, methylene chloride, or a mixture thereof.

The reaction temperature is not critical and the reaction is preferably conducted within the range of cooling to an ambient temperature.

The compound (V) can be used as the starting compound in the next step, Step C, without isolation or purification.

Step C

The compound (VI) or a salt thereof can be produced by reacting the compound (V) with thiourea.

This reaction is usually conducted in a conventional solvent which does not adversely influence the reaction such as ethyl acetate, methylene chloride, chloroform, carbon tetrachloride, tetrahydrofuran, N,N-dimethylformamide, N,N-dimethylacetamide, dioxane, water, acetic acid, formic acid, etc. or a mixture thereof.

The reaction temperature is not critical and the reaction is usually conducted under cooling to warming.

Step D

The compound (I) or a salt thereof can be produced by subjecting the compound (VI) or a salt thereof to the removal reaction of the carboxy-protective group.

Suitable salt of the compound (VI) may include the same acid addition salt as exemplified for the compound (I).

Suitable method for this removal reaction may include conventional one such as hydrolysis, reduction, or the like.

(i) For hydrolysis:

Hydrolysis is preferably carried out in the presence of an acid.

Suitable acid may be an inorganic acid (e.g. hydrochloric acid, hydrobromic acid, sulfuric acid, etc.), an organic acid (e.g. formic acid, acetic acid, trifluoroacetic acid, propionic acid, methanesulfonic acid, benzenesulfonic acid, p-toluenesulfonic acid, etc.), an acidic ion-exchange resin and the like. In case that the organic acid such as trifluoroacetic acid and p-toluenesulfonic acid is used in this reaction, the reaction is preferably carried out in the presence of cation trapping agents (e.g. anisole, etc.).

Further, instead of the above acid, Lewis acid such as boron trifluoride, boron trifluoride etherate, aluminum trichloride, antimony pentachloride, ferric chloride, stannic chloride, titanium tetrachloride, zinc chloride, and the like can be also used in this reaction, and in case of using Lewis acid, the reaction can preferably be carried out in the presence of cation trapping agent (e.g. anisole).

The hydrolysis is usually conducted in a conventional solvent which does not adversely influence the reaction such as methylene chloride, water, methanol, ethanol, propanol, tert-butyl alcohol, tetrahydrofuran, N,N-dimethylformamide, N,N-dimethylacetamide, dioxane or a mixture thereof, and further the above-mentioned acids can be also used as a solvent when they are in liquid.

The reaction temperature of this hydrolysis is not critical, and the reaction is usually conducted under cooling to warming.

(ii) For Reduction:

Reduction is conducted in a conventional manner, including chemical reduction and catalytic reduction.

Suitable reducing agents to be used in chemical reduction are a combination of a metal (e.g. tin, zinc, iron, etc.) or metallic compound (e.g. chromium chloride, chromium acetate, etc.) and an organic or inorganic acid (e.g. formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g. platinum plate, spongy platinum, platinum black, colloidal platinum, platinum oxide, platinum wire, etc.), palladium catalysts (e.g. spongy palladium, palladium black, palladium oxide, palladium on carbon, colloidal palladium, palladium on barium sulfate, palladium on barium carbonate, etc.), nickel catalysts (e.g. reduced nickel, nickel oxide, Raney nickel, etc.), cobalt catalysts (e.g. reduced cobalt, Raney cobalt, etc.), iron catalysts (e.g. reduced iron, Raney iron, etc.), copper catalysts (e.g. reduced copper, Raney copper, Ullman copper, etc.) and the like.

The reduction is usually conducted in a conventional solvent which does not adversely influence the reaction such as water, methanol, ethanol, propanol, N,N-dimethylformamide, or a mixture thereof.

Additionally, in case that the above-mentioned acids to be used in chemical reduction are in liquid, they can be also used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually conducted under cooling to warming.

Step E

The compound (VII) or a salt thereof can be produced by subjecting the compound (V) to the removal reaction of the carboxy-protective group.

Suitable salts of the compound (VII) may include the same salt with a base as exemplified for the compound (I).

The removal reaction of the carboxy-protective group in this step can be carried out according to a similar manner to that explained in Step D.

Step F

The compound (I) or a salt thereof can be produced by reacting the compound (VII) or a salt thereof with thiourea.

This reaction can be carried out according to a similar manner to that explained in Step C.

In case that the compound (I) obtained by means of aforesaid process is in free form, it can be converted to its salt form, especially to its acid addition salt according to a conventional manner and in case that the compound (I) obtained is in salt form, it can be converted to its free form according to a conventional manner (Please make reference to References 1 to 4 described later).

Further, the compound (I) obtained according to aforesaid process can be converted to Crystal A of the present invention by applying the method to prepare said crystal disclosed before during the isolation step of the compound (I).

The process explained above in the one which gives the compound (I) in high yield and this process can be carried out very safely. Said process is also suitable for preparing the compound (I) in a large scale.

In the following, the present invention is explained in more detail according to Preparations and Examples.

Preparation 1

Benzhydryl 7-amino-3-vinyl-3-cephem-4-carboxylate hydrochloride (26.6 kg) was dissolved in N,N-dimethylacetamide (78 l) and then this solution was cooled to −10° C.

A solution of 4-chloroacetoacetyl chloride in methylene chloride, which was prepared by bubbling chlorine (6.5 kg) into a solution of diketene (7.6 kg) in methylene chloride (130 l) below −25° C., was added dropwise to the solution obtained above at −10°∼0° C. with stirring. After the addition, the stirring was continued at the same temperature for 30 minutes.

After the reaction, the reaction mixture was diluted with methylene chloride (130 l) at 5° C. with stirring, then 6% sodium bicarbonate aqueous solution (260 l) was added thereto with stirring and then the organic layer was separated. The organic layer was washed with water (156 l) at 5° C. The organic layer was concentrated in vacuo to the volume of 182 l and then acetone (130 l) was added thereto and the solution was concentrated in vacuo again to the volume of 182 l. To the concentrated solution, acetone (78 ) was added and then methanol (130 l) was added dropwise at 20° C. After stirring for 10 minutes, water (260 l) was added thereto and this solution was cooled to 5° C. with stirring, then allowed to stand overnight.

The resultant crystals were collected by filtration, washed with 30% aqueous methanol (130 l) and then dried to give benzhydryl 7-(4-chloroacetoacetamido)-3-vinyl-3-cephem-4-carboxylate (31.3 kg).

mp: 171° C.

IR (Nujol): 3260, 1775, 1713, 1661, 1224, 698 cm$^{-1}$.

NMR (DMSO-d$_6$, δ): 9.18 (1H, d, J=8 Hz), 7.6–7.1 (10H, m), 6.98 (1H, s , 6.76 (1H, dd, J=18 Hz and 11 Hz), 5.80 (1H, dd, J=8 Hz and 5 Hz), 5.63 (1H, d, J=18 Hz), 5.30 (1H, d, J=11 Hz), 5.22 (1H, d, J=5 Hz), 4.59 (2H, s), 3.93 and 3.60 (2H, ABq, J=18 Hz), 3.61 (2H, s).

Preparation 2

Benzhydryl 7-(4-chloroacetoacetamido)-3-vinyl-3-cephem-4-carboxylate (30.8 kg) was suspended in methylene chloride (290 l) and this suspension was cooled to −5° C. After cooling, 10.6 N hydrogen chloride in tetrahydrofuran solution (267 ml) was added thereto, then isoamyl nitrite (7.1 kg) was added and the resultant mixture was stirred for 60 minutes at 0° C.

The resultant solution of benzhydryl 7-(4-chloro-2-hydroxyiminoacetoacetamido)-3-vinyl-3-cephem-4-carboxylate in methylene chloride was added to a solution of thiourea (6.5 kg) in N,N-dimethylacetamide (78 l) for 1 hour together with concentration of the reaction solution in vacuo. After methylene chloride was removed, the mixture was stirred for 30 minutes at 50° C. After the reaction was over, acetone (145 l) and 5% sodium bicarbonate aqueous solution (73 l) were added thereto at 20° C. and the resultant solution was added dropwise to water (290 l) for 20 minutes with keeping the temperature of the solution at 20° C. After this addition, the resultant solution was adjusted to pH 6 with 5% sodium bicarbonate aqueous solution, cooled to 5° C. with stirring and then allowed to stand overnight.

The resultant precipitates were collected by filtration, washed with 40% aqueous acetone (145 l) and dried to give benzhydryl 7-[2-(2-aminothiazol-4-yl)-2-hydroxyiminoacetamido]-3-vinyl-3-cephem.-4-carboxylate (syn isomer)(36.9 kg).

IR (Nujol): 3320, 1782, 1720, 1670, 1618, 1528, 1220, 698 cm$^{-1}$.

NMR (DMSO-d$_6$, δ): 11.31 (1H, s), 9.58 (1H, d, J=8 Hz), 7.6–7.2 (10H, m), 7.14 (2H, broad s), 6.98 (1H, s), 6.79 (1H, dd, J=18 Hz and J=11 Hz), 6.72 (1H, s), 5.92 (1H, dd, J=8 Hz and 5 Hz), 5.67 (1H, d,J=18 Hz), 5.31

(1H, d, J=11 Hz), 5.29 (1H, d, J=5 Hz), 3.93 and 3.60 (2H, ABq, J=18 Hz).

Preparation 3

Benzhydryl 7-amino-3-vinyl-3-cephem.-4-carboxylate hydrochloride (68.9 g) and bis(trimethylsilyl)urea (103 g) were dissolved in tetrahydrofuran (700 ml) and the solution was cooled to −25° C. To this solution 4-chloroacetoacetyl chloride, which was obtained by reacting a solution of diketene (17.9 g) in methylene chloride (50 ml) with a solution of chlorine (14.9 g) in carbon tetrachloride (100 ml) at −40° ~ −30° C., was added slowly at −25° C. and the mixture was stirred for 1 hour at −15° C. The reaction mixture was poured into a mixture of ethyl acetate (900 ml) and water (900 ml). The organic layer was separated and washed with sodium chloride aqueous solution (700 ml). Solvent was removed and to the resultant crystals isopropyl ether (700 ml) was added and the mixture was stirred for 1 hour under ice-cooling. The crystals were collected by filtration and dried to give benzhydryl 7-(4-chloroacetoacetamido)-3-vinyl-3-cephem-4-carboxylate (72.5 g).

NMR (CDCl$_3$, δ): 3.55 (2H, ABq, J=18 Hz), 3.60 (2H, s), 4.17 (2H, s), 4.99 (1H, d, J=5 Hz), 5.27 (1H, d, J=11 Hz), 5.42 (1H, d, J=17 Hz), 5.81 (1H, dd, J=5 Hz and 8 Hz), 6.95 (1H, s), 7.00 (1H, dd, J=11 Hz and 17 Hz), 7.10–7.53 (10H, m).

Preparation 4

To a solution of benzhydryl 7-(4-chloroacetoacetamido)-3-vinyl-3-cephem-4-carboxylate (5.0 g) in methylene chloride (45 ml) and acetic acid (16.5 ml) was added dropwise a solution of sodium nitrite (1.35 g) in water (2.5 ml) at −20° C. and then the mixture was stirred for 8 minutes. Ethyl acetoacetate (1.27 g) was added thereto and the mixture was stirred for 5 minutes, then the reaction solution was washed with water 3 times. The organic solvent was removed to give a residue, which was triturated with diisopropyl ether. The resultant solid was collected by filtration and dried to give benzhydryl 7-(4-chloro-2-hydroxyiminoacetoacetamido)-3-vinyl-3-cephem.-4-carboxylate (4.36 g).

IR (Nujol): 3260, 1765, 1705, 1650, 1540 cm$^{-1}$.

NMR (CDCl$_3$, δ): 3.60 (2H, broad s), 4.74 (2H, s), 5.09 (1H, d, J=5 Hz), 5.33 (1H, d, J=11 Hz), 5.49 (1H, d, J=17 Hz), 5.80 (1H, dd, J=5 Hz, and 8 Hz), 6.99 (1H, s), 7.10 (1H, dd, J=11 Hz and 17 Hz), 7.18–7.57 (10H, m), 9.38 (1H, d, J=8 Hz).

Preparation 5

Benzhydryl 7-(4-chloro-2-hydroxyiminoacetoacetamido)-3-vinyl-3-cephem.-4-carboxylate (25.0 g) was dissolved in a mixture of methylene chloride (150 ml) and anisole (15 ml). To the resultant solution was added dropwise 2,2,2-trifluoroacetic acid (500 ml) at 5° C. with stirring, then the mixture was stirred for 30 minutes.

The reaction solution was concentrated in vacuo and the resultant residue was triturated with diisopropyl ether (250 ml) to give a solid product (16.5 g). This product was dissolved in isopropyl alcohol (80 ml) and dealt with activated charcoal (1.6 g), then the solution was allowed to stand at 5° C. for 3 hours. The resultant precipitates were collected by filtration to give colorless crystals (7.8 g)(This crystal contains one molecule of isopropyl alcohol).

The resultant crystals (6.0 g) were recrystallized from a mixture of ethanol (25 ml) and water (50 ml) to give 7-(4-chloro-2-hydroxyiminoacetoacetamido)-3-vinyl3-cephem-4-carboxylic acid (3.4 g).

mp 134°–138° C. (decomp.).

IR (Nujol): 3350, 3450, 3250, 1770, 1700, 1665, 1540 cm$^{-1}$.

NMR (DMSO-d$_6$, δ): **3.83 and 3.57 (2H, ABq, J=18 Hz), 5.80 (2H, s), 5.17 (1H, d, J=5 Hz), 5.30 (1H, J=11 Hz), 5.57 (1H, d, J=17 Hz), 5.78 (1H, dd, J=8 Hz and J=5 Hz), 6.88 (1H, dd, J=17 Hz and J=11 Hz), 9.28 (1H, d, J=8 Hz), 13.08 (1H, s).

The Preparation Of Crystal A Of The Compound (I)

EXAMPLE 1

7-[2-(2-Aminothiazol-4-yl)-2-hydroxyiminoacetamido]-3-vinyl-3-cephem.-4-carboxylic acid (syn isomer)(an amorphous product)(29.55 g) was added to water (300 ml) and the mixture was adjusted to pH 6.0 with saturated sodium bicarbonate aqueous solution. The resultant solution was subjected to a column chromatography on activated charcoal and eluted with 20% aqueous acetone. The fractions were combined and concentrated to a volume of 500 ml. The resultant solution was adjusted to pH 1.8 at 35° C. with 4N hydrochloric acid. The resultant precipitates were collected by filtration, washed with water and dried to give 7-[2-(2-aminothiazol-4-yl)-2-hydroxyiminoacetamido]-3-vinyl-3-cephem-4-carboxylic acid (syn isomer)(19.29 g) as crystals (Crystal A).

IR (Nujol): 1760, 1670, 1620 cm$^{-1}$.

EXAMPLE 2

To a solution of 7-[2-(2-aminothiazol-4-yl)-2-hydroxyiminoacetamido]-3-vinyl-3-cephem-4-carboxylic acid (syn isomer)(an amorphous product)(0.5 g) in methanol (10 ml) was added dropwise warm water (35° C.; 1.5 ml) at 35° C. and the resultant solution was stirred slowly for 3 minutes, then allowed to stand at room temperature. The resultant crystals were collected by filtration, washed with water and then dried to give 7-[2-(2-aminothiazol-4-yl)-2-hydroxyiminoacetamido]-3-vinyl-3-cephem-4-carboxylic acid (syn isomer) as crystals (Crystal A)(0.4 g).

IR (Nujol): 1760, 1670, 1620 cm$^{-1}$.

In the following, powder X-ray diffraction pattern of this Crystal A was shown.

The measurement condition was as follows.

| Target: Cu | Filter: Ni |
|---|---|
| Voltage: 30 kv | Current: 10 mA |
| Detector: Scintillation Counter | |

| 2 θ(°) | relative intensity |
|---|---|
| 11.7 | 18 |
| 12.5 | 15 |
| 14.7 | 76 |
| 16.6 | 16 |
| 17.8 | 56 |
| 18.9 | 22 |
| 19.1 | 16 |
| 21.5 | 100 |
| 22.0 | 70 |
| 23.4 | 38 |
| 24.4 | 80 |
| 25.3 | 22 |
| 26.9 | 10 |
| 27.6 | 22 |
| 28.0 | 40 |

| | |
|---|---|
| 29.6 | 18 |

EXAMPLE 3

Benzhydryl 7-[2-(2-aminothiazol-4-yl)-2-hydroxyiminoacetamido]-3-vinyl-3-cephem-4-carboxylate (syn isomer)(35 kg) was suspended in anisole (239 l) and this suspension was cooled to −10° C. 98% formic acid (3.3 kg) and 47% boron trifluoride etherate (54 kg) were added thereto at the same temperature, then the mixture was stirred for 40 minutes at −1°~1° C.

To the reaction solution, acetone cooled to −10° C. (199 l) was added. By adding dropwise both this solution and 12% sodium hydroxide aqueous solution to a mixture cooled at −10° C. of water (265 ) and acetone (212 l) at the same time with stirring, the neutralization reaction was carried out in the range from pH 4 to 6 at −10°~0° C.

After neutralization, the mixture was allowed to stand, then aqueous layer was separated. Aqueous layer was washed with ethyl acetate (106 l). After the aqueous layer was washed with ethyl acetate (106 l) again, it was concentrated in vacuo to the volume of 557 l. The concentrated solution was adjusted to pH 3.7 with 17.5% hydrochloric acid at 20° C. to precipitate the crystals. This mixture was cooled to 5° C. with stirring, then stirred overnight. The resultant crystals were collected by filtration, washed with water (133 l) and dried to give crude crystals of 7-[2-(2-aminothiazol-4-yl)-2-hydroxyiminoacetamido]-3-vinyl-3-cephem-4-carboxylic acid (syn isomer)(Crystal A)(17.3 kg).

IR (Nujol): 3295, 1767, 1683, 1620, 1518, 1013 cm$^{-1}$.

NMR (DMSO-d$_6$, δ) 11.27 (1H, broad s , 9.53 (1H, d, J=8 Hz), 7.11 (2H, broad s), 6.96 (1H, dd, J=18 Hz and 11 Hz), 6.70 (1H, s), 5.80 (1H, dd, J=8 Hz and 5 Hz), 5.60 (1H, d, J=18 Hz), 5.31 (1H, d, J=11 Hz), 5.20 (1H, d, J=5 Hz), 3.87 and 3.53 (2H, ABq, J=18 Hz).

EXAMPLE 4

A suspension of crude crystals of 7-[2-(2-aminothiazol-4-yl)-2-hydroxyiminoacetamido]-3-vinyl3-cephem-4-carboxylic acid (syn isomer)(Crystal A) obtained in aforesaid Example 3 (21.1 kg) in water (255 l) was cooled to 5° C. Sodium bicarbonate (2.7 kg) was added thereto at 5° C. and dissolved under reduced pressure with degassing. The resultant solution was subjected to a column chromatography on nonionic adsorption resin "Diaion HP-20" (51 l) Trademark:manufactured by Mitsubishi Chemical Industries). The eluate obtained above was then subjected to a column chromatography on γ-alumina (25.5 l) and eluted with 3% sodium acetate aqueous solution. The resultant eluate was adjusted to pH 3.5 at 21°-25° C. with 17.5% hydrochloric acid and then the crystals were crystallized out of the solution by the addition of 17.5% hydrochloric acid with keeping the pH of the solution at 3.5. The resultant suspension containing the crystals was cooled to 5° C. and stirred overnight. The crystals were collected by filtration, washed with water (42.5 l) and dried in vacuo at 35° C. to give 7-[2-(2-aminothiazol-4-yl)-2-hydroxyiminoacetamido]-3-vinyl-3-cephem-4-carboxylic acid (syn isomer)(6.7 kg) as crystals (Crystal A).

IR (Nujol): 1765, 1685, 1620 cm$^{-1}$.

In the following, powder X-ray diffraction pattern of this Crystal A was shown. The measurement condition was the same that was used in Example 2.

| 2 θ (°) | relative intensity |
|---|---|
| 11.8 | 15 |
| 12.6 | 16 |
| 14.7 | 66 |
| 16.6 | 16 |
| 17.8 | 49 |
| 18.9 | 24 |
| 19.2 | 18 |
| 21.5 | 100 |
| 22.0 | 66 |
| 23.4 | 38 |
| 24.5 | 77 |
| 25.4 | 20 |
| 26.9 | 8 |
| 27.7 | 18 |
| 28.1 | 36 |
| 29.7 | 15 |

EXAMPLE 5

7-(4-Chloro-2-hydroxyiminoacetoacetamido)-3-vinyl-3-cepham-4-carboxylic acid (373.8 mg) was added to a mixture of thiourea (76 mg), sodium acetate (82 mg) and water (5 ml). The pH value of the reaction mixture was maintained from 5.5 to 5.7 during the reaction by the addition of 1.4% ammonium hydroxide aqueous solution. The reaction mixture was stirred at room temperature for 4 hours, then thiourea (38 mg) was added thereto and the mixture was stirred further for 2 hours.

The yellowish reaction mixture was filtered by passing it through a column packed with acidic aluminium oxide (5.0 g) [Elution was carried out by using 1% sodium acetate buffer solution (pH 6.0)]. The eluate was adjusted to pH 3.3 with 10% hydrochloric acid, then stirred slowly for 1 hour at room temperature. The resultant crystals were collected by filtration, washed with small amount of cold water and dried in vacuo over phosphorus pentoxide to give 7-[2-(2-aminothiazol-4-yl)-2-hydroxyiminoacetamido]-3-vinyl-3-cephem-4carboxylic acid (syn isomer) as crystals (Crystal A) (239 mg)

mp: 182°-187° C. (decomp.).

IR (Nujol): 3350, 3300, 1770, 1690, 1630, 1600, 1560, 1520 cm$^{-1}$.

NMR (DMSO-d$_6$, δ): 3.57 and 3.83 (2H, ABq, J=18 Hz), 5.18 (1H, d, J=5 Hz), 5.33 (1H, d, J=11 Hz), 5.60 (1H, d, J=17 Hz), 5.80 (1H, dd, J=8 Hz and J=5 Hz), 6.70 (1H, s), 7.03 (1H, dd, J=11 Hz and J=17 Hz), 7.08 (2H, broad s), 9.43 (1H, d, J=8 Hz).

In the following References 1 to 4, the various salts of the compound (I) are given.

Reference 1

To a suspension of 7-[2-(2-aminothiazol-4-yl)-2-hydroxyiminoacetamido]-3-vinyl-3-cephem-4-carboxylic acid (syn isomer)(4.26 g) in water (26 ml) was added conc. hydrochloric acid (4.26 ml) at room temperature, then the mixture was stirred under ice-cooling for 1 hour. The solvent was removed by decantation and resultant oily precipitates were triturated with diethyl ether, acetone and n-hexane. The resultant powder was collected by filtration to give 7-[2-(2-aminothiazol-4-yl)-2-hydroxyiminoacetamido]-3-vinyl-3-cephem-4-carboxylic acid hydrochloride (syn isomer)(4.30 g).

IR (Nujol): 3200, 1760-1780, 1720, 1660-1680, 1625 cm$^{-1}$.

NMR (DMSO-d$_6$, δ): 3.70 (2H, ABq, J=18 and 26 Hz), 5.22 (1H, d, J=5 Hz), 5.30 (1H, d, J=11 Hz), 5.75

(1H, dd, J=8 and 5 Hz), 5.59 (1H, d, J=17 Hz), 6.85 (1H, s), 6.70-7.17 (2H, m), 9.67 (1H, d, J=8 Hz), 12.3 (1H, broad s).

Reference 2

To a suspension of 7-[2-(2-aminothiazol-4-yl)-2-hydroxyiminoacetamido]-3-vinyl-3-cephem-4-carboxylic acid (syn isomer)(0.4 g) in ethyl acetate (2 ml) and ethanol (2 ml) was added ethyl acetate solution containing sulfuric acid at 10% (0.54 ml) under ice-cooling, then the reaction mixture was stirred under ice-cooling for 1 hour. To the reaction mixture was added diethyl ether (40 ml) and the mixture was further stirred under ice-cooling for 1 hour. The resultant precipitates were collected by filtration, washed with diethyl ether and dried in vacuo to give sulfuric acid salt of 7-[2-(2-aminothiazol-4-yl)-2-hydroxyiminoacetamido]-3-vinyl-3-cephem-4-carboxylic acid (syn isomer)(0.48 g).

IR (Nujol): 1765, 1750, 1720, 1660, 1640 cm$^{-1}$.

NMR (DMSO-d$_6$, δ): 3.73 (2H, ABq, J=18 Hz and 26 Hz), 5.21 (1H, d, J=5 Hz), 5.0-5.90 (3H, m), 6.89 (1H, s), 6.70-7.17 (2H, m), 9.69 (1H, d, J=8 Hz).

Reference 3

To a suspension of 7-[2-(2-aminothiazol-4-yl)-2-hydroxyiminoacetamido]-3-vinyl-3-cephem-4-carboxylic acid (syn isomer)(0.5 g) in methanol (2 ml) was added a solution of methanesulfonic acid (0.158 g) in methanol (0.5 ml) at 0°-5° C., then the mixture was stirred at the same temperature for 1 hour. The reaction mixture was added dropwise to ethanol and the resultant precipitates were collected by filtration to give methanesulfonic acid salt of 7-[2-(2-aminothiazol-4-yl)-2-hydroxyiminoacetamido]-3-vinyl-3-cephem-4-carboxylic acid (syn isomer) (0.56 g).

IR (Nujol): 1760-1780, 1630-1670, 1590, 1520 cm$^{-1}$.

NMR (DMSO-d$_6$, δ) 2.40 (3H, s), 3.72 (2H, ABq, J=18 Hz and 26 Hz), 5.22 (1H, d, J=5 Hz), 5.30 (1H, d, J=11 Hz), 5.59 (1H, d, J=17 Hz), 5.60-5.90 (1H, m), 6.86 (1H, s), 6.67-7.17 (2H, m), 9.67 (1H, d, J=8 Hz), 12.2 (1H, broad s).

Reference 4

To an aqueous solution (40 ml) of 3-(N-formyl-N-hydroxyamino)propylphosphonic acid (0.43 g) was added 7-[2-(2-aminothiazol-4-yl)-2-hydroxyiminoacetamido]-3-vinyl-3-cephem-4-carboxylic acid (1.0 g) with vigorous stirring, then the mixture was stirred at room temperature for 5 hours. The reaction mixture was lyophilized to give a hygroscopic solid. This solid was dissolved in methanol (10 ml), then the resultant solution was added dropwise to diethyl ether (500 ml) under cooling. The resultant precipitates were collected by filtration to give 3-(N-formyl-N-hydroxyamino)propylphosphonic acid salt of 7-[2-(2-aminothiazol-4-yl)-2-hydroxyiminoacetamido]-3-vinyl-3-cephem-4-carboxylic acid (syn isomer)(0.50 g) as powder.

NMR (D$_2$O, δ): 1.39-2.20 (4H, m), 3.47-3.87 (4H, m), 5.27 (1H, d, J=5 Hz), 5.30-5.73 (2H, m), 5.80 (1H, d, J=5 Hz), 6.95 (1H, dd, J=17 Hz and J=20 Hz), 7.11 (1H, s), 7.94, 8.29 (total 1H, each s).

What we claim is:

1. Crystalline 7-[2-(2-aminothiazol-4-yl)-2-hydroxyiminoacetamido]-3-vinyl-3-cephem.-4-carboxylic acid (syn isomer) which shows the peaks at the diffraction angles shown in the following table in its powder X-ray diffraction pattern:

| diffraction angle(°) |
| --- |
| about 14.7 |
| about 17.8 |
| about 21.5 |
| about 22.0 |
| about 23.4 |
| about 24.5 |
| about 28.1 |

2. Crystalline 7-[2-(2-aminothiazol-4-yl)-2-hydroxyiminoacetamido]-3-vinyl-3-cephem-4-carboxylic acid (syn isomer) which is obtainable by acidifying a solution containing 7-[2-(2-aminothiazol-4-yl)-2-hydroxyiminoacetamido]-3-vinyl-3-cephem-4-carboxylic acid (syn isomer) at room temperature or under warming.

3. Crystalline substance of claim 2, wherein a solution containing 7-[2-(2-aminothiazol-4-yl)-2-hydroxyiminoacetamido]-3-vinyl-3-cephem-4-carboxylic acid (syn isomer) is an aqueous solution of an alkali metal salt of said compound.

4. Crystalline substance of claim 3, wherein the acidifying of the solution is carried out at the temperature from room temperature to 40° C. at the pH from 1 to 4.

5. Crystalline 7-[2-(2-aminothiazol-4-yl)-2-hydroxyiminoacetamido]-3-vinyl-3-cephem-4-carboxylic acid (syn isomer) which is obtainable by dissolving 7-[2-(2-aminothiazol-4-yl)-2-hydroxyiminoacetamido]-3-vinyl-3-cephem-4-carboxylic acid (syn isomer) in an alcohol, continuing to stir the solution slowly under warming, then cooling the solution to room temperature and allowing the solution to stand.

* * * * *

UNITED STATES PATENT AND TRADEMARK OFFICE

CERTIFICATE EXTENDING PATENT TERM UNDER 35 U.S.C. § 156

| | | |
|---|---|---|
| PATENT NO. | : | 4,935,507 |
| ISSUED | : | June 19, 1990 |
| INVENTORS | : | Takao Takaya, et al. |
| PATENT OWNER | : | Fujisawa Pharmaceutical Co., Ltd. |
| PRODUCT | : | OMNICEF® Oral Suspension (cefdinir) |

This is to certify that an application under 35 U.S.C. § 156 has been filed in the U.S. Patent and Trademark Office, requesting extension of the term of U.S. Patent No. 4,935,507 based upon the regulatory review of the product OMNICEF® Oral Suspension (cefdinir) by the Food and Drug Administration. Since it appears that the requirements of the law have been met, this certificate extends the term of the patent for the period of 1,213 days from August 8, 2008, the original expiration date of the patent, subject to the provisions of 35 U.S.C. § 41(b), with all rights pertaining thereto as provided by 35 U.S.C. § 156(b).

I have caused the seal of the U.S. Patent and Trademark Office to be affixed this 19th day of January 2001.

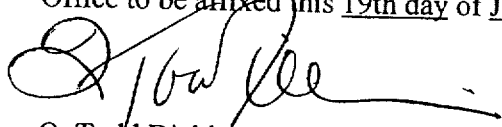

Q. Todd Dickinson
Under Secretary of Commerce for Intellectual Property and Director of the United States Patent and Trademark Office